(12) United States Patent
Clark et al.

(10) Patent No.: US 11,617,616 B2
(45) Date of Patent: Apr. 4, 2023

(54) CONFIGURABLE CONTROL HANDLE FOR CATHETERS AND OTHER SURGICAL TOOL

(71) Applicant: Biosense Webster (Israel) Ltd., Yokneam (IL)

(72) Inventors: Jeffrey L. Clark, Castaic, CA (US); Adam Molina, Irvine, CA (US); Luan Truong, Irvine, CA (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 794 days.

(21) Appl. No.: 16/558,768

(22) Filed: Sep. 3, 2019

(65) Prior Publication Data
US 2020/0015887 A1    Jan. 16, 2020

Related U.S. Application Data

(63) Continuation of application No. 13/902,639, filed on May 24, 2013, now Pat. No. 10,398,499.

(51) Int. Cl.
*A61B 18/00* (2006.01)
*A61B 18/14* (2006.01)
(Continued)

(52) U.S. Cl.
CPC ..... *A61B 18/1492* (2013.01); *A61M 25/0097* (2013.01); *A61B 2018/00029* (2013.01);
(Continued)

(58) Field of Classification Search
CPC ...... A61B 18/1492; A61B 2018/00029; A61B 2018/0091; A61B 90/08; A61M 25/0097;
(Continued)

(56) References Cited

U.S. PATENT DOCUMENTS 3,438,534 A    4/1969 Zerwes
4,417,890 A *  11/1983 Dennehey ............. A61M 39/20
                                                      604/905
(Continued)

FOREIGN PATENT DOCUMENTS

CN    101073505 A    11/2007
CN    101918068 A    12/2010
(Continued)

OTHER PUBLICATIONS

English Translation of Chinese Examination Report for Chinese Application No. 201410221787 4, dated Jun. 13, 2017, 6 pages.
(Continued)

*Primary Examiner* — Katherine H Schwiker
*Assistant Examiner* — Phoebe Anne Staton
(74) *Attorney, Agent, or Firm* — Etan S. Chatlynne; Calderon Safran & Cole, P.C.

(57) ABSTRACT

A control handle for a surgical tool, e.g., an irrigated ablation catheter for use with a fluid side arm, has a housing defining an interior cavity and having a port through which the component can extend into the interior cavity. The housing has a detachable plug covering at least a portion of the port and being at least partially surrounded by a recessed groove to facilitate detachment of the plug from the housing. The recessed groove may be formed on an outer surface of the housing and there may be a second recessed groove on an inner surface of the housing generally tracing the first groove. The plug may also include a hinge to allow the plug to be arranged at an angled position relative to the housing without being fully detached from the housing.

8 Claims, 5 Drawing Sheets

(51) Int. Cl.
*A61M 25/00* (2006.01)
*A61M 25/01* (2006.01)

(52) U.S. Cl.
CPC .. *A61B 2018/0091* (2013.01); *A61M 25/0136* (2013.01); *A61M 25/0147* (2013.01)

(58) Field of Classification Search
CPC .......... A61M 25/0136; A61M 25/0147; A61M 25/01; A61M 2025/0018; B65D 77/2048
See application file for complete search history.

(56) References Cited

U.S. PATENT DOCUMENTS

| | | | |
|---|---|---|---|
| 5,139,500 | A | 8/1992 | Schwartz |
| 5,207,644 | A | 5/1993 | Strecker |
| 5,407,436 | A | 4/1995 | Toft et al. |
| 5,556,377 | A * | 9/1996 | Rosen .................. A61N 1/06 604/22 |
| 5,672,153 | A * | 9/1997 | Lax .................. A61B 10/0275 604/22 |
| 6,522,930 | B1 | 2/2003 | Schaer et al. |
| 6,699,243 | B2 | 3/2004 | West et al. |
| 8,235,396 | B2 | 8/2012 | Keene et al. |
| 8,475,522 | B2 | 7/2013 | Jimenez et al. |
| 2002/0049391 | A1 | 4/2002 | Kuracina et al. |
| 2011/0282176 | A1 | 11/2011 | Tegg |
| 2012/0039764 | A1 * | 2/2012 | Solomon ............. A61M 39/162 422/292 |
| 2012/0046610 | A1 | 2/2012 | Rankin |
| 2012/0238819 | A1 | 9/2012 | Long et al. |

FOREIGN PATENT DOCUMENTS

| | | |
|---|---|---|
| CN | 102429719 A | 5/2012 |
| CN | 202459790 U | 10/2012 |
| JP | 2006043131 A | 2/2006 |
| JP | 2011507606 A | 3/2011 |
| WO | 03084428 A2 | 10/2003 |
| WO | 03101522 A1 | 12/2003 |
| WO | 2011008812 A2 | 1/2011 |
| WO | 2012154235 A1 | 11/2012 |
| WO | 2012162259 A2 | 11/2012 |

OTHER PUBLICATIONS

Extended European Search Report for European Application No. 14169635.1, dated Aug. 26, 2014, 5 pages.
Extended European Search Report for European Application No. 18202082.6, dated Nov. 30, 2018, 11 pages.

* cited by examiner

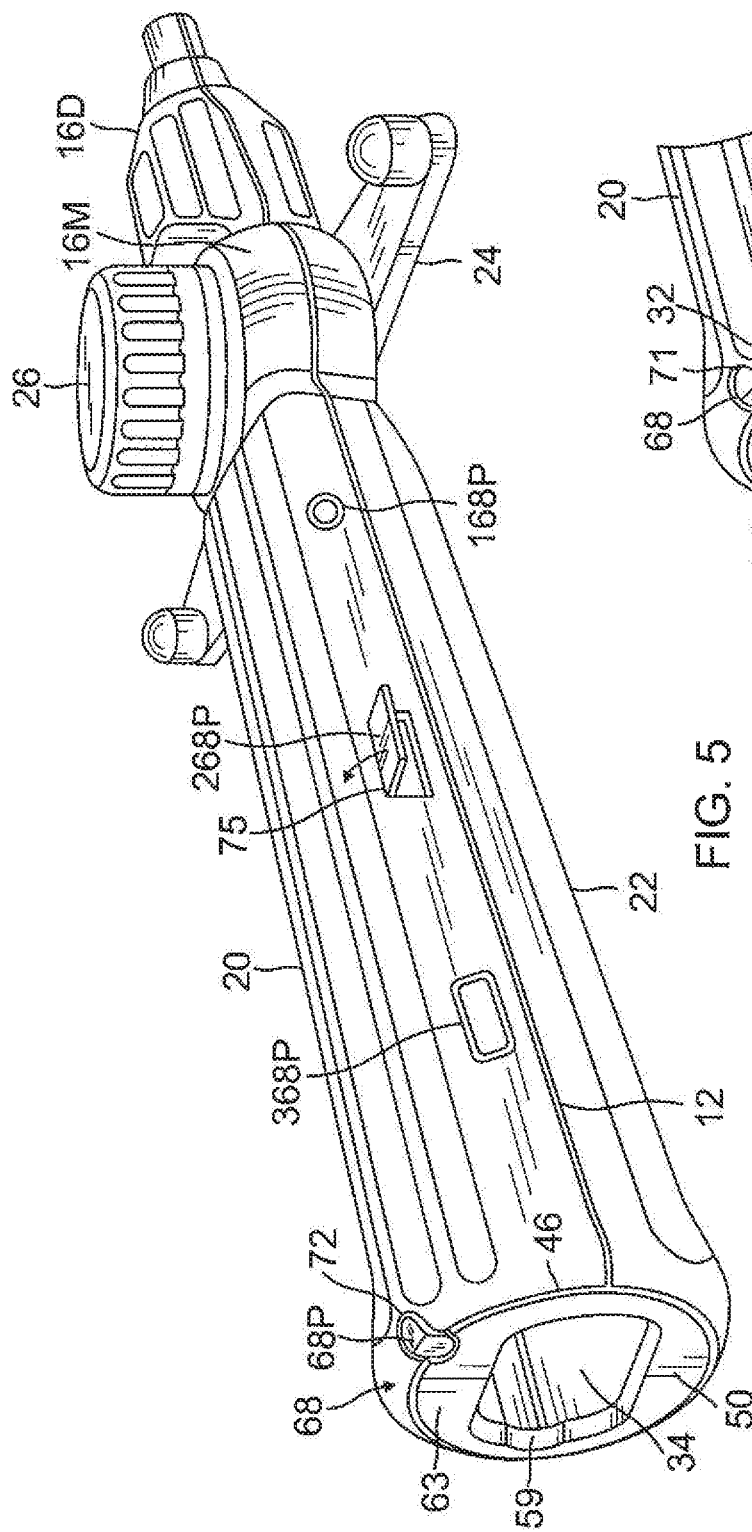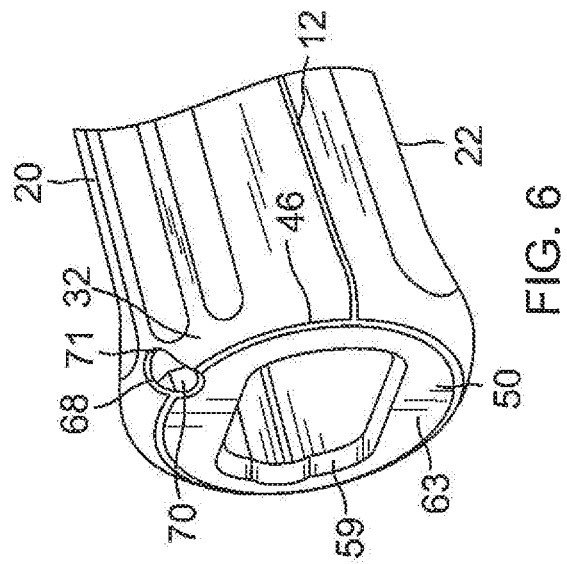

CONFIGURABLE CONTROL HANDLE FOR CATHETERS AND OTHER SURGICAL TOOL

CROSS-REFERENCE TO COPENDING APPLICATION

The present application is a Continuation under 35 U.S.C. § 120 of U.S. patent application Ser. No. 13/902,639, filed May 24, 2013. The entire contents of this application is incorporated by reference herein in their entirety.

FIELD OF INVENTION

This invention relates to a control handle, in particular, a control handle for a medical device, including a catheter.

BACKGROUND

Electrode catheters have been in common use in medical practice for many years. They are used to stimulate and map electrical activity in the heart and to ablate sites of aberrant electrical activity. Depending on the procedure, the catheter may be used with or without irrigation, that is, with or without fluid, e.g., saline, delivered to a distal section of the catheter to irrigate a tissue target site. Where irrigation is desired, a conventional control handle of a catheter may be used with a side arm connected to a luer hub in fluid communication with a fluid source, where the side arm extends into the control handle. To that end, housing of the control handle has an opening or hole for the side arm. Where irrigation is not desired, the housing of a suitable control handle may be identical except for the hole. But, despite the close structural similarity of these two types of control handles, two sets of capital tool molds are needed in the manufacture of these handles, with each type requiring independent qualifications and stocking of inventory. The requirement for separate parts places additional burden on the supply chain because both configurations are kept as safety stock as insurance against marketing forecast revisions.

Using handle housings with uncovered holes for constructing either nonirrigated and irrigated catheters is possible but there are shortcomings. Functionally, an uncovered hole can increase the risk of contamination, damage and/or failure of electronics and components internal the control handle. Aesthetically, an uncovered hole presents an undesirable appearance of an unfinished or damaged product.

Accordingly, there is a desire for a medical device control handle that can be assembled and configured for multiple uses, including irrigated and nonirrigated catheter-based procedures. A configurable handle would allow a single part number to serve multiple roles and would require configuration only at the time of assembly, thereby reducing part number proliferation and inventory carrying costs.

SUMMARY OF THE INVENTION

The present invention is directed to a control handle for a medical or surgical tool configurable for use selectively with or without a component. In one embodiment, the control handle has a housing defining an interior cavity and having a port through which the component can extend into the interior cavity. In accordance with a feature of the present invention, the housing has a detachable plug covering at least a portion of the port and being at least partially surrounded by a recessed groove to facilitate detachment of the plug from the housing. The recessed groove may be formed on an outer surface of the housing and there may be a second recessed groove on an inner surface of the housing generally tracing the first groove. The plug may also include a hinge to allow the plug to be oriented at an angled position relative to the housing without being fully detached from the housing. In a more detailed embodiment, the surgical tool comprises an irrigated ablation catheter and the component comprises a fluid side arm.

In another embodiment, the control handle is for a catheter adapted for use with an irrigation side arm. The control handle includes a housing defining an interior cavity and providing a port for the irrigation side arm and a detachable plug covering the port.

In another embodiment, the control handle includes a housing, a receptacle and a port. The housing has a proximal housing opening in communication with an interior cavity. The receptacle is inserted into the interior cavity via the proximal housing opening and has a proximal end with a peripheral flange that merges with a surrounding edge of the proximal opening of the control handle housing. The port overlaps the surrounding edge of the control handle and the peripheral flange of the receptacle so that it extends partially on one side into the surrounding edge and partially on the other side into the peripheral flange. The port is covered by a detachable plug formed in the handle housing and may include a main portion and a finger extending at an angle from the main portion.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 5 is a perspective view of a control handle with a covered proximal port and additional distal ports, in accordance with another embodiment of the present invention.

FIG. 6 is a perspective view of the control handle of FIG. 5, with the proximal port uncovered.

DETAILED DESCRIPTION OF THE INVENTION

Figure 1:
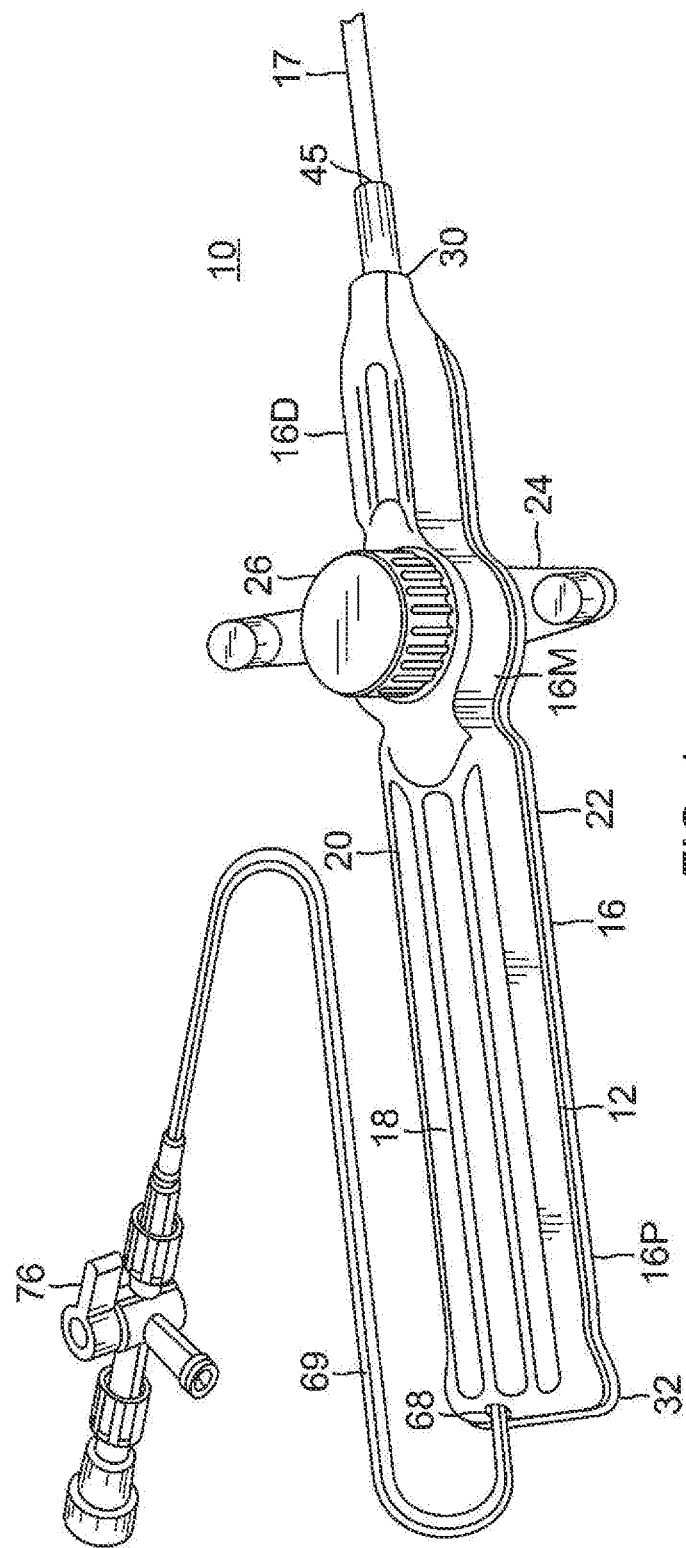
FIG. 1 is a perspective view of a control handle in accordance with an embodiment of the present invention.

Referring to FIG. 1, the present invention is directed to a control handle 16 for assembly and use with a catheter 10 or other medical devices and surgical tool handles, wherein housing (or a portion thereof) is configurable to provide one or more openings allowing the control handle to be adapted for different uses and applications. In the illustrated embodiment of FIG. 1, a control handle 16 comprises an elongated housing with two generally similar halves 20 and 22 that are affixed, e.g., by sonic welding, laser welding, adhesives and/or the like, to each other along a longitudinal seam 12.

The control handle is configured for one-handed operation. The handle has a proximal portion 16P, a mid portion 16M and a distal portion 16D between a distal end 30 and a proximal end 32. The proximal portion 16P is configured with a textured, friction-inducing surface 18 to be gripped by the user's hand. The mid-portion 16M has a deflection knob 24 on the housing half 22 for controlling deflection of a catheter distal tip section and a tension knob 26 on the housing half 20 for adjusting tension of the deflection knob. The distal portion 16D has a tapered profile leading to a catheter shaft 17 that extends distally from the distal end 30 of the control handle 16.

Figure 2:
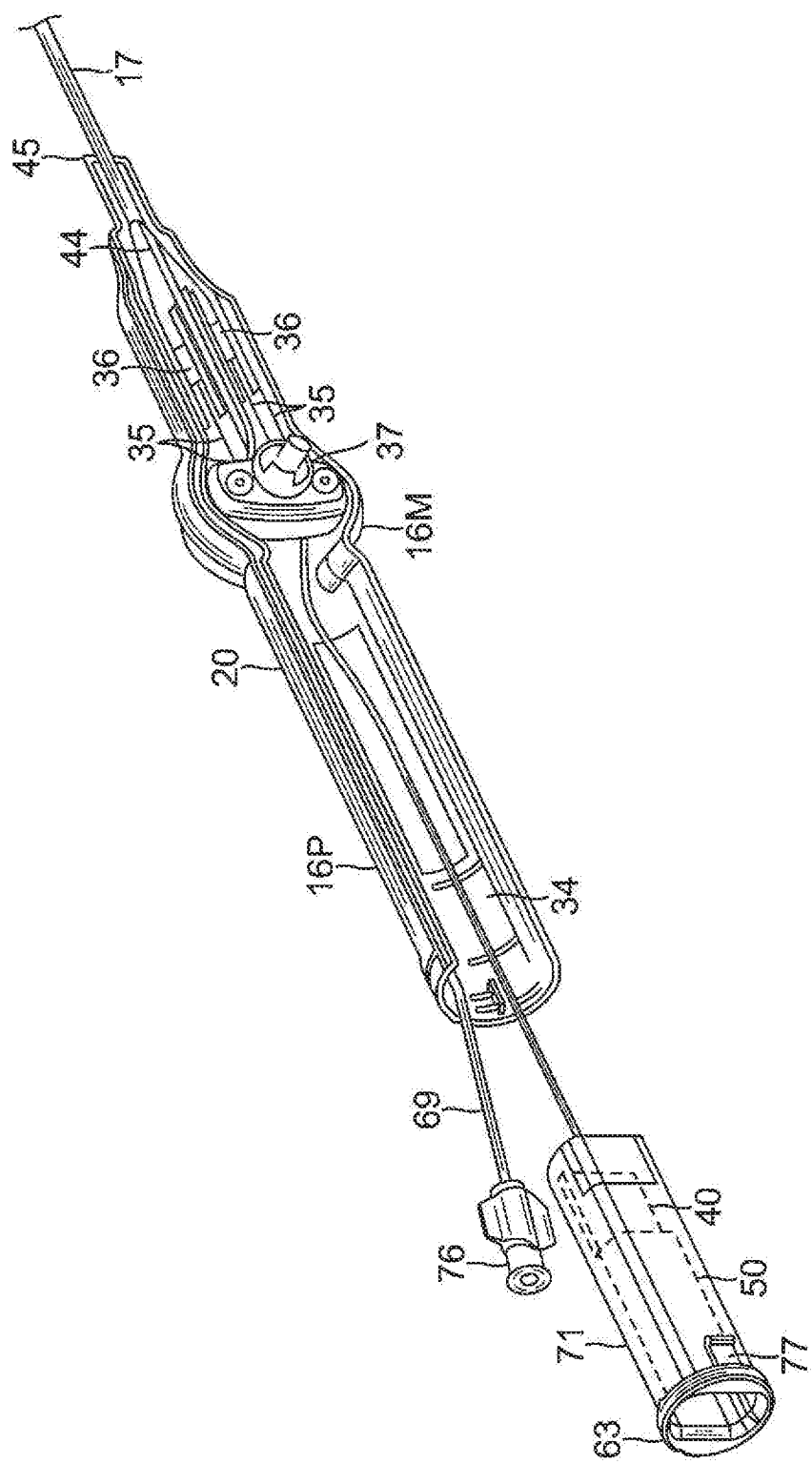
FIG. 2 is an exploded, partial side cross-sectional view of the control handle of FIG. 1.
Figure 4:
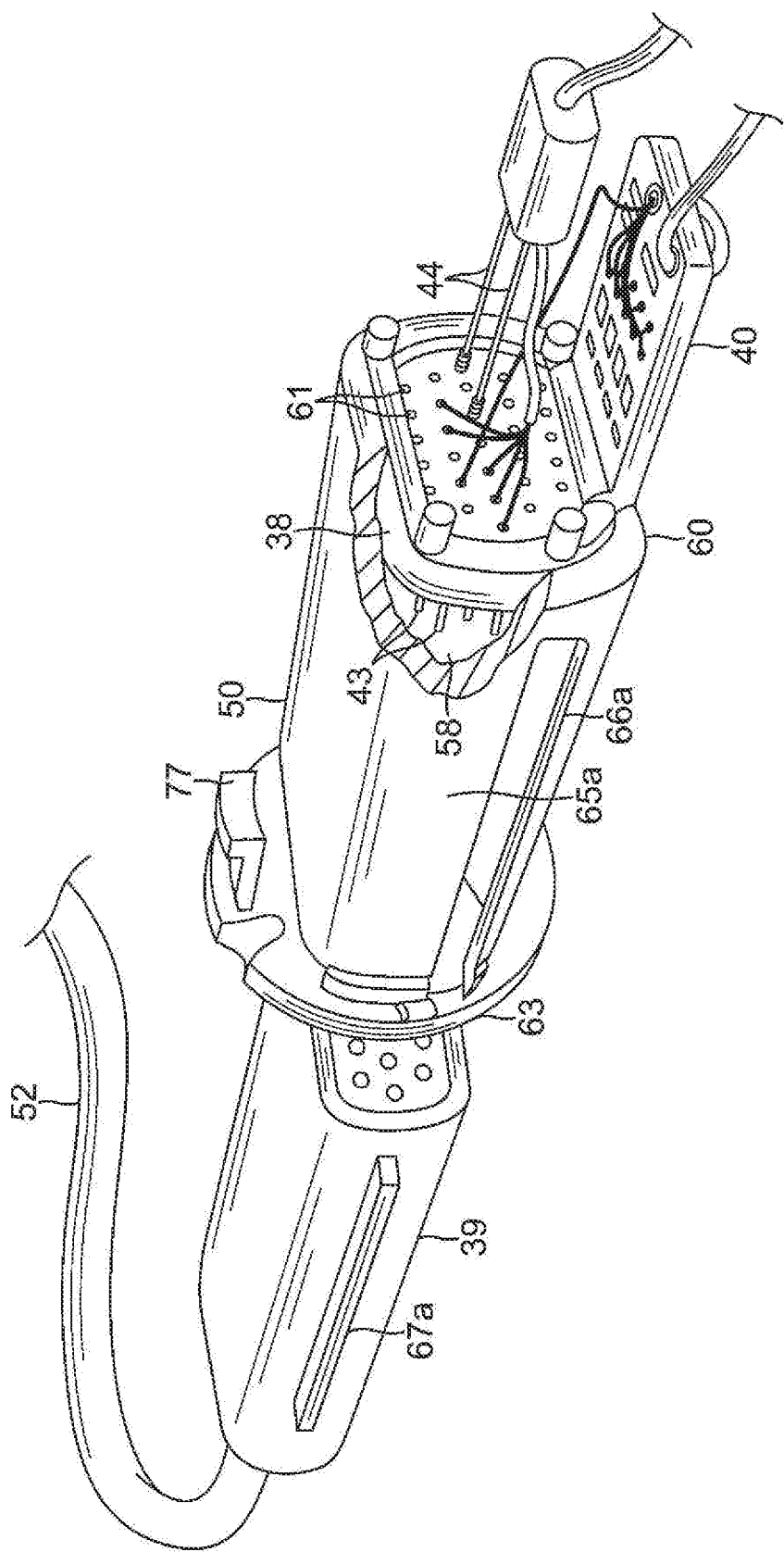
FIG. 4 is a perspective view of a receptacle with a circuit board, and an electrical connector, in accordance with one embodiment of the present invention.

As shown in FIG. 2, the housing defines an interior cavity 34 between the housing half 20 and the housing half 22 (not shown). As shown in FIGS. 2 and 4, components housed in or near mid-portion 16M of the control handle include puller wires 35, anchoring members 36 for proximal ends of the puller wires, and a deflection assembly 37 responsive to the deflection knob 24. Components housed in or near the proximal-portion 16P of the control handle include a first electrical connector 38 and a circuit board 40 connected thereto by connector leads 42. The circuit board 40 performs function(s) including amplifying signals received from electromagnetic sensor(s) (not shown) carried on the catheter distal tip section, and transmitting them to a computer in a form understandable by a computer (not shown). The circuit board 40 may also contain an EPROM chip which shuts down the circuit board after the catheter has been used. This prevents the catheter, or at least the electromagnetic sensors, from being used twice. Also connected to the first electrical connector 38 are proximal ends of electrode lead wires 44 extending into the control handle 16 from the distal end 30. Distal ends of the wires 44 are connected to tip and/or ring electrodes (not shown) mounted on the distal tip section of the catheter.

As shown in FIG. 2, the distal end 30 of the control handle has an opening 45 through which the catheter shaft 17 extends. Extending through the shaft 17 are components, including electrode lead wires 44, the puller wires 35, electromagnetic position sensor cable and irrigation tubing. With reference to FIGS. 3 and 4, the proximal end 32 of the control handle has an opening 46 configured to receive a receptacle 50 that facilitates coupling of an electrical umbilical cord 52 with a second electrical connector 39 adapted for connection to the first electrical connector 38 housed in the control handle 16. In the illustrated embodiment, the first electrical connector 38 is a male connector with pins 43 positioned at a distal end of the receptacle 50 and the second electrical connector 39 is a female socket, although it is understood that the connector structures may be reversed. The electrical umbilical cord 52 connects the catheter 10 to a patient interface unit (not shown) which communicates with an electroanatomical navigation system (not shown), e.g., CARTO available from Biosense Webster of Irwindale, Calif., which is a 3-D mapping system that provides electrophysiologists with magnetic location technology and visualization data of catheter tip and curve location, anatomical mapping with rapid creation of high-resolution, CT-like maps. The patient interface unit functions as a central connection between the electroanatomical navigation system and the catheter 10.

As shown in FIGS. 3 and 4, the receptacle 50 has a body defining a distal cavity portion 58, and a proximal opening 59 through which the second electrical connector 39 is inserted and received in the distal cavity portion 58. A distal end surface 60 of the receptacle 50 has a plurality of openings 61 through which electrical leads 42 are connected to pins 43 extending proximally within the cavity portion 58 for connection with the second electrical connector 39. The proximal opening 59 of the receptacle 50 has a surrounding flange 63 which is adapted to generally seal the proximal opening 46 of the control handle when the receptacle 50 (along with the second electrical connector 39) is inserted into the proximal opening 46 (FIG. 5). To that end, alignment formations are formed in or on the receptacle 50 to ensure the electrical connector 39 is "keyed" and inserted into the receptacle 50 with the correct alignment and/or orientation. In the illustrated embodiment, asymmetrical slots 66a and 66b of different lengths are provided in side walls 65a and 65b, respectively, that match and correspond, respectively, with asymmetrical ridges 67a and 67b formed on opposite outer surfaces of the electrical connector 39. As shown in FIG. 2, a sleeve shield 71 may be provided outside of the receptacle 50 in surrounding relationship therewith to shield the circuit board 40. The shield may be made of any suitable material, for example, Mu-metal, a range of nickel-iron alloys that are notable for their high magnetic permeability, composed of approximately 77% nickel, 16% iron, 5% copper and 2% chromium or molybdenum. The high permeability makes Mu-metal useful for shielding against static or low-frequency magnetic fields. To lock the receptacle 50 in the control handle 16, a flexible flanged tab 77 is provided extending distally from a distal surface of the peripheral flange 63, which engages a ridge formation provided on an inner surface of the housing half 22.

Where the catheter 10 is assembled for irrigated procedures, the control handle housing 16 is configurable to provide a closely-conforming port 68, as better shown in FIGS. 1 and 5, to allow an irrigation side arm 69 to extend into the interior cavity of the control handle. As shown in FIG. 6, the port 68 is formed on one side in one part by a recessed formation 70 in the peripheral flange 63 of the receptacle 50, and on the opposite side in another part by a recessed formation 71 in the proximal end 32 of the housing half 20 at the periphery of the proximal opening 46, when the receptacle 50 is received in the handle housing.

In accordance with a feature of the present invention, the control handle housing 20 is configurable to provide a covered port 68 where the catheter 10 is assembled for nonirrigated procedures or procedures that do not require an accessory component extending into the control handle. As shown in FIGS. 3 and 5, the control handle housing presents a generally closed proximal end with an aesthetically complete appearance by means of a pre-defined section or detachable "plug" 68P of the handle housing that can be selectively removed or retained during assembly of the control handle.

Figure 3A:
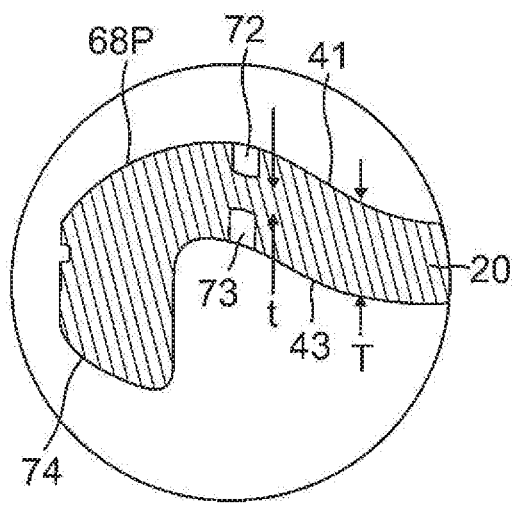
FIG. 3A is a cross-sectional view of the control handle of FIG. 3, taken along line A-A.
Figure 3:
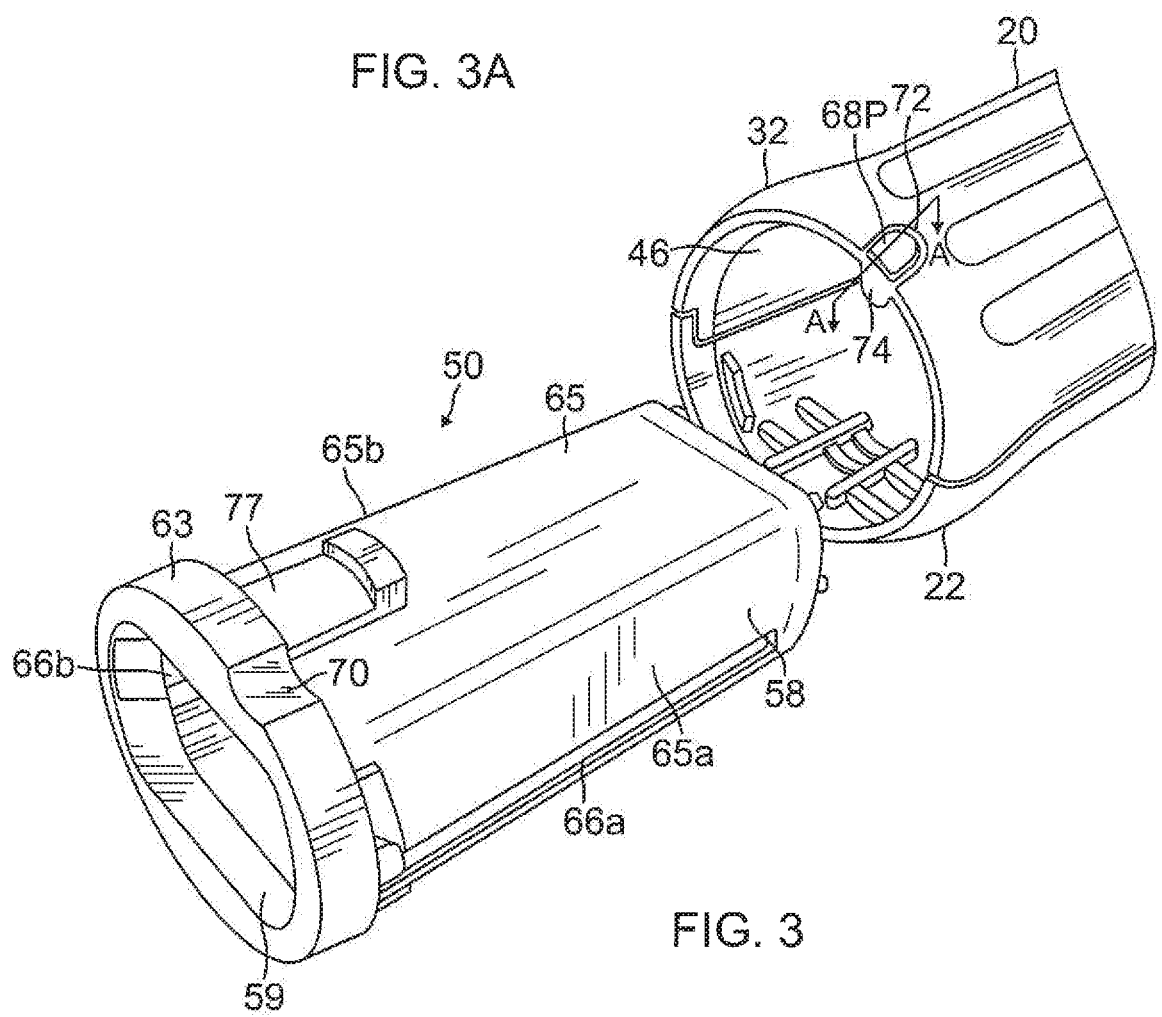
FIG. 3 is a detailed exploded perspective view of a distal end of the control handle of FIG. 1.

With reference to FIGS. 3 and 3A, the plug 68P has a defined peripheral boundary in the form of a recessed groove 72 that extends around the plug 68P on an outer surface 41 of the handle housing half 20. In the illustrated embodiment of FIG. 3, the defined peripheral boundary or groove 72 surrounds a portion of the plug 68P, for example, about 180 degrees, although it is understood that a defined peripheral boundary may surround a plug in varying degrees, ranging between about 0 to 360 degrees, depending on the location and/or configuration of the plug and the control handle. For example, the defined peripheral boundary may completely surround (by 360 degrees) a plug 168P or plug 368P and be located more distally in/on the control handle housing half 20 or 22, as shown in FIG. 5. It is understood that the plug may be located anywhere on the housing and assume any shape, e.g., circular, oval, rectangular, polygonal and/or irregular, as appropriate or needed. As shown in FIG. 3A, the groove 72 has a thickness t less than the thickness T of the surrounding housing so that the plug can be readily knocked out, punched out, broken off or otherwise detached (manually and/or with a tool) and removed from the handle housing. The groove 72 also provides a visual indication of its location, shape and size. A second matching groove 73 (FIG. 3A) that generally traces the groove 72 may be provided on an inner surface of the handle housing to further decrease the thickness t between the grooves 72 and 73 and further facilitate the detachment of the plug from the housing.

In the illustrated embodiment of FIGS. 3 and 3A, the plug 68P has a finger 74 that extends inwardly at an angle (e.g., about 90 degrees). The finger 74 may serve multiple functions, including covering the recessed formation 70 in the flange 63 of the receptacle 50 to completely cover the port 68 (FIG. 5) and/or facilitate detachment of plug 68P to expose the port (FIG. 6).

It is understood that the plug 68P need not necessarily be detachable or removable from the handle housing half 20. As illustrated in FIG. 5, the plug 268P may have a hinge 75 that allows the plug 268P to be positioned at varying angles (see arrow) relative to the handle housing half 20 to expose the port or cover the port.

In use, the housing halves 20 and 22 are joined to form the control handle 10. In doing so, a determination is made as to whether the control handle is for assembly with an irrigated catheter or a non-irrigated catheter so that a person assembling the control handle can decide whether to remove the plug 68P from the housing halve 20 or leave the port 68 and plug 68P intact and the port 68 covered. Although the plug 68P may be removed before the housing halves 20 and 22 are joined, the plug may also be removed afterwards. The plug may be removed in any suitable manner, including being pried off, punched through or cut, which may be accomplished, manually and/or with an appropriate tool. The grooves 72 and 73 facilitate detachment of the plug from the housing half 20. Preferably, the plug 69P detaches from the housing half 20 along a boundary defined by the grooves 72 and 73. In the embodiment of FIG. 1, the removal of the plug 68P exposes the port 68, allowing an irrigation side arm 69 to enter the interior cavity 34 of the control handle 16. A distal end of the side arm 69 is connected to a luer hub 76 in fluid communication with a fluid source (not shown) which provides fluid, e.g., saline, travelling through an irrigation tubing extending through the control handle and the distal portion of the catheter where it exits the catheter at the tissue treatment site. Alternatively, where the port and plug remain intact, the control handle presents an aesthetically pleasing appearance of a finished and undamaged product.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. For example, the catheter can be adapted such that the third puller member advances and retracts another component such as a guide wire or a needle. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:

1. A control handle for a surgical tool, comprising:
 a first housing half comprising a plug including a finger, the first housing half including a peripheral boundary that extends around a portion of the plug on an outer surface of the first housing half;
 a second housing half affixed to the first housing half such that the first housing half and second housing half together define a housing having a proximal end, an interior cavity, and a proximal opening disposed through the proximal end; and
 a receptacle disposed through the proximal opening and at least partially disposed in the interior cavity, the receptacle including a peripheral flange defining a recessed formation in which the finger is disposed,
 in which the proximal opening comprises a first portion that is defined by the first housing half and a second portion that is defined by the second housing half.

2. The control handle of claim 1, in which the peripheral boundary comprises a first groove that surrounds at least a portion of the plug.

3. The control handle of claim 2, in which the first groove comprises a first reduced thickness portion of the first housing half.

4. The control handle of claim 3, in which a second groove surrounds at least another portion of the plug on an inner surface of the first housing half such that the second groove comprises a second reduced thickness portion of the first housing half.

5. The control handle of claim 1, in which the plug and first housing half are connected by a hinge.

6. The control handle of claim 1, in which the finger extends away from the first housing half at an angle of about 90 degrees.

7. The control handle of claim 1, in which the plug covers a port into the interior cavity.

8. The control handle of claim 1, in which the plug is detachable from a rest of the first housing half along the peripheral boundary such that, upon detachment of the plug, a port into the interior cavity is partially defined by the recessed formation.

\* \* \* \* \*